United States Patent
Mueh et al.

(10) Patent No.: US 9,618,466 B2
(45) Date of Patent: Apr. 11, 2017

(54) USE OF SPECIFIC RESISTIVITY MEASUREMENT FOR INDIRECT DETERMINATION OF THE PURITY OF SILANES AND GERMANES AND A CORRESPONDING PROCESS

(75) Inventors: Ekkehard Mueh, Rheinfelden (DE); Hartwig Rauleder, Rheinfelden (DE); Rainer Amend, Otzberg (DE); Martin Hajduk, Goldbach (DE)

(73) Assignee: Evonik Degussa GmbH, Essen (DE)

( * ) Notice: Subject to any disclaimer, the term of this patent is extended or adjusted under 35 U.S.C. 154(b) by 1239 days.

(21) Appl. No.: 13/580,843

(22) PCT Filed: Dec. 28, 2010

(86) PCT No.: PCT/EP2010/070805
§ 371 (c)(1),
(2), (4) Date: Nov. 7, 2012

(87) PCT Pub. No.: WO2011/103941
PCT Pub. Date: Sep. 1, 2011

(65) Prior Publication Data
US 2013/0043893 A1  Feb. 21, 2013

(30) Foreign Application Priority Data
Feb. 25, 2010 (DE) .................. 10 2010 002 342

(51) Int. Cl.
*C23C 16/00* (2006.01)
*G01N 27/04* (2006.01)
*G01N 33/00* (2006.01)

(52) U.S. Cl.
CPC ..... *G01N 27/04* (2013.01); *G01N 2033/0095* (2013.01)

(58) Field of Classification Search
CPC . G01N 27/04; G01N 2033/0095; C23C 16/22
(Continued)

(56) References Cited

U.S. PATENT DOCUMENTS 4,042,331 A * 8/1977 Schmidt ................. G01N 31/00
                                                        422/83
6,142,024 A   11/2000 Rauleder et al.
(Continued)

FOREIGN PATENT DOCUMENTS

DE   1 523 001   4/1969
DE   25 58 183   7/1977
(Continued)

OTHER PUBLICATIONS

A. Yusa, "Analyzer of trace impurities in silane gas", Rev. Sci. Instrum., vol. 47, No. 2, Feb. 1976, 4 pages.
(Continued)

*Primary Examiner* — Kelly M Gambetta
(74) *Attorney, Agent, or Firm* — Oblon, McClelland, Maier & Neustadt, L.L.P.

(57) ABSTRACT

The invention relates to a method for indirectly determining the purity of silanes and germanes using a device for measuring specific resistance. The invention further relates to a system for industrially producing and/or filling containers with silanes or germanes, including a quality control in which a device is used for measuring specific resistance.

18 Claims, 2 Drawing Sheets

(58) Field of Classification Search
USPC .................................................. 427/248.1, 8
See application file for complete search history.

(56) References Cited

U.S. PATENT DOCUMENTS

| | | | |
|---|---|---|---|
| 6,585,941 | B2 | 7/2003 | Zehe et al. |
| 8,002,954 | B2 | 8/2011 | Popp et al. |
| 8,038,961 | B2 | 10/2011 | Sonnenschein et al. |
| 8,221,593 | B2 | 7/2012 | Lang et al. |
| 8,246,925 | B2 | 8/2012 | Schwarz et al. |
| 2009/0117717 | A1* | 5/2009 | Tomasini ............... C23C 16/04 438/488 |
| 2010/0080746 | A1 | 4/2010 | Lang et al. |
| 2010/0266489 | A1 | 10/2010 | Rauleder et al. |
| 2010/0270296 | A1 | 10/2010 | Rauleder et al. |
| 2010/0274028 | A1 | 10/2010 | Mueh et al. |
| 2010/0278706 | A1 | 11/2010 | Mueh et al. |
| 2010/0296994 | A1 | 11/2010 | Rauleder et al. |
| 2011/0052474 | A1 | 3/2011 | Mueh et al. |
| 2011/0150739 | A1 | 6/2011 | Seliger et al. |
| 2011/0184205 | A1 | 7/2011 | Rauleder et al. |
| 2012/0177557 | A1 | 7/2012 | Rauleder et al. |
| 2012/0183464 | A1 | 7/2012 | Mueh et al. |
| 2012/0195804 | A1 | 8/2012 | Lang et al. |
| 2012/0214005 | A1 | 8/2012 | Wieber et al. |

FOREIGN PATENT DOCUMENTS

| | | |
|---|---|---|
| JP | 62-145149 | 6/1987 |
| JP | 5-335245 | 12/1993 |
| JP | 2002-234721 A | 8/2002 |

OTHER PUBLICATIONS

U.S. Appl. No. 13/884,326, filed May 9, 2013, Mueh, et al.
U.S. Appl. No. 14/383,757, filed Sep. 8, 2014, Mueh, et al.
U.S. Appl. No. 13/985,477, filed Aug. 14, 2013, Mueh, et al.
Taylor, et al., "Purification Techniques and Analytical Methods for Gaseous and Metallic Impurities in High-Purity Silane," Journal of Crystal Growth, vol. 89 No. 1, p. 28, (Jun. 1, 1988).
International Search Report Issued Jun. 15, 2011 in PCT/EP10/70805 Filed Dec. 28, 2010.

* cited by examiner

USE OF SPECIFIC RESISTIVITY MEASUREMENT FOR INDIRECT DETERMINATION OF THE PURITY OF SILANES AND GERMANES AND A CORRESPONDING PROCESS

The present invention relates to a process for indirectly determining the purity of silanes and germanes using an instrument for measuring specific resistivity. The invention further relates to a plant for industrial production and/or dispensing of silanes or germanes, including a quality control step in which an instrument for measuring specific resistivity is used.

The determination of the content of impurities in generally gaseous precursor compounds which are used for demanding applications in the semiconductor or solar industry is difficult, since the possible detection and determination limits of, for example, ICP-MS or ICP-OES are insufficient for this purpose. More particularly, the content of impurities resulting from elements of main group 3 of the elements of the periodic table (known as p-type impurities) and of main group 5 (known as n-type impurities) is critical, for example, for semiconductor and solar cell products which have silicon or germanium layers which are produced from the precursor compounds mentioned, for example by deposition in CVD or similar processes.

Given that quality control with respect to impurities resulting from elements of main groups 3 and 5 of the elements of the periodic table has to date been difficult or impossible within the detection range actually necessary for silicon or germanium precursor compounds, it is not surprising that there has to date been no routine quality control carried out as standard for this purpose, in the sense of more or less permanent monitoring of the purity of the compounds produced and/or dispensed, in the continuous operation of an industrial production process and/or dispensing process for silanes or germanes.

It was an object of the present invention to provide a process for quality control of silanes and germanes, especially for monitoring the purity with respect to the elements of main groups 3 and 5 of the periodic table of the elements, and the process should be suitable for enabling quality control in the sense of real-time or timely monitoring in continuous operation of an industrial production process and/or dispensing process for silanes or germanes. More particularly, the process should be suitable for detecting and quantifying extremely low concentrations of impurities resulting from elements of main groups 3 and 5 of the periodic table of the elements, since ultrahigh purity demands are made on silanes and germanes, which are used, for example, in the semiconductor industry or the solar cell industry, and customers from this sector desire evidence of quality, especially with respect to the elements of main groups 3 and 5 mentioned.

This object is achieved in accordance with the invention by a process for indirectly determining the purity of silanes and germanes, characterized in that a silicon layer or germanium layer is produced on a surface from the silane or germane by deposition from the gaseous state, then the specific resistivity of the layer produced is measured and the value measured, using reference values determined beforehand, is used to conclude the purity of the silane or germane used to produce the layer.

The process thus envisages that the impurities are not determined directly by methods applied to the silanes or germanes, but indirectly by measuring a physical property of a silicon or germanium layer which is produced from the silanes or germanes in question, said physical property, namely the specific resistivity, being crucially influenced by the concentration of the impurities in the silanes or germanes used, and which get into the layer in the course of the deposition process. Especially impurities relating from elements of main groups 3 and 5 of the periodic table of the elements influence the specific resistivity of the silicon or germanium layer.

The specific resistivity (short for specific electrical resistivity) is a temperature-dependent material constant with the symbol $\rho$. The electrical resistivity of a conductor with a constant cross-sectional area (section at right angles to the longitudinal axis of a body) over its length is: $R=\rho A/l$, where R is the electrical resistance, $\rho$ is the specific resistivity, l is the length and A is the cross-sectional area of the conductor. Consequently, $\rho$ can be determined from the measurement of the resistivity of a conductor piece of known geometry.

In the context of the present invention, the resistivity and the layer thickness are measured by means of the SRP (spreading resistance probe) method. For this purpose, a piece of the coated wafer is ground down to the substrate at a defined angle. The resistivity is then measured by means of two probe tips which scan the entire profile at particular distances and in each case give a resistivity at a particular layer thickness. The grinding angle and the path length can also be used to calculate the layer thickness. The method is described in detail in several standards and stipulates the procedure described above. The methods used here follow the SEMI standards MF672 and MF674, to which reference is made in MF672. The SEMI standard MF672 is an extension of the SEMI standard MF525. The SEMI standards are also published as ASTM standards (e.g. ASTM F 672-80).

Since the process according to the invention may be of great benefit for the industrial sector in particular, preferred silanes and germanes are those which are used on the industrial scale. Preference is therefore given to the silanes and germanes selected from the unsubstituted mono-, di- or trisilanes or the unsubstituted mono-, di- or trigermanes or the singly, multiply or fully halogen-substituted mono-, di- or trisilanes or the singly, multiply or fully halogen-substituted mono-, di- or trigermanes. Particular preference is given to $SiH_4$, $SiH_3Cl$, $SiH_2Cl_2$, $SiHCl_3$, $SiCl_4$, $Si_2H_6$, $Si_2Cl_6$, $Si_3H_8$, $Si_3Cl_8$, $GeH_4$ and $GeCl_4$.

As already mentioned, especially impurities resulting from elements of main groups 3 and 5 of the periodic table of the elements influence the specific resistivity of the otherwise ultrahigh-purity silicon or germanium layer. The term "purity" therefore preferably relates to the minimal concentration of elements from main groups 3 and 5 of the periodic table of the elements in the layers analysed, and hence also in the silanes or germanes used to produce these layers. Impurities resulting from elements from main group 3 of the periodic table of the elements are referred to as p-type impurities, and impurities resulting from elements from main group 5 as n-type impurities.

In the simplest case, the indirect determination of the purity of the silanes or germanes analysed can be effected qualitatively, in the sense that, with reference to the specific resistivity measured, a statement is possible to the effect that the silane or germane used has a predetermined minimum degree of "purity", i.e. is more or less pure with respect to impurities which influence the specific resistivity relative to a reference silane or germane.

Furthermore, the process according to the invention also enables, by correspondingly careful preparation of reference values and reference curves, which are described in detail below, a relatively exact quantitative determination of the purity of the silane or germane used.

In one embodiment of the process according to the invention, it is possible to conclude the total content of elements of main groups 3 and 5 of the periodic table of the elements, without these elements being attributed to either main group.

In another embodiment of the process according to the invention, the purity can relate to the total content of elements of main group 3 of the periodic table of the elements on the one hand and/or main group 5 of the periodic table of the elements on the other hand, attribution of the impurities to either main group also being possible.

In the process according to the invention, the deposition from the gaseous state onto the surface is preferably effected by a CVD process onto a silicon wafer in the case of determination of the purity of silanes, and onto a germanium wafer in the case of determination of the purity of germanes.

In the CVD processes, silicon- or germanium-based precursors or mixtures of precursors are evaporated in suitable reactors (e.g. Applied Centura HAT, ASM Epsilon 2000 or Novellus Concept One 200) and deposited on hot surfaces (for example a silicon wafer) to give the solid layer material. More recent modifications to this process, for example RPCVD (reduced pressure chemical vapour deposition), LPCVD (low pressure chemical vapour deposition) and PECVD (plasma enhanced pressure chemical vapour deposition) have also been found to be advantageous, enabling more rapid deposition at in some cases significantly reduced temperature (literature: Andreas Weber, "Chemical vapour deposition—Eine Übersicht", Spektrum der Wissenschaft, April 1996, 86-90).

Useful substrates include commercially available silicon and germanium wafers. Diameter: 1-12 inch, Czochralski or Float-zone type, p- or n-predoped, orientation <100> or <111> must be shown in the calibration, specific resistivity 0.001-15000 $\Omega$cm. It is possible to use single- or double-sidedly polished wafers. The wafers are normally heated in an $H_2$ stream in an epitaxy reactor for a short time before the coating, generally 0.5-5 min, in order to remove the natural oxide layer. This is followed by the deposition step without removal of the wafer from the chamber.

To determine the final value of the specific resistivity which is established from a certain layer thickness, the silicon layer or the germanium layer in the case of a doped wafer having a specific resistivity of <1000 $\Omega$cm should have a thickness of 5 to 100 µm, preferably 8 to 50 µm, more preferably 10 to 20 µm, and in the case of a lightly doped wafer having a specific resistivity of >1000 $\Omega$cm (for example in the case of flow-zone wafers) should have a thickness of 1 to 50 µm, preferably 2 to 25 µm, more preferably 3 to 10 µm. This minimum thickness guarantees that the specific resistivity measured generally no longer changes significantly as the layer continues to grow, and is then influenced exclusively by the gas to be deposited. The thicknesses are determined with the aid of the measuring instrument described in the SEMI standards.

In a particular embodiment, the process according to the invention can be configured such that the determination of the purity of the silanes or germanes can be performed repeatedly for the purposes of continuous monitoring of purity, corresponding to real-time or timely monitoring. This variant is suitable especially in the course of industrial production and/or industrial dispensing of these silanes and germanes. In this case, it is possible to branch off or withdraw suitable amounts of the silane or germane at regular intervals from the normal process streams, and send them to epitaxy and subsequent analysis. The advantages over sampling from previously filled bottles are: no change of bottle or container for each new batch, no possibility of contamination when the bottle is changed, and continuous process control.

When the process according to the invention is performed for the purposes of continuous monitoring, it comprises at least the following steps:

a) preparing or providing the silane or germane, b) branching off or withdrawing a suitable amount of the silane or germane, c) producing a silicon or germanium layer from at least a portion of the branched-off or withdrawn amount of silane or germane by a CVD process on a silicon wafer or germanium wafer, d) measuring the specific resistivity on the surface of the layer produced, and e) attributing the specific resistivity measured to a degree of purity without attributing the contaminating elements to one of the main groups of the periodic table of the elements, the degree of purity preferably being reported as a concentration.

The suitable amount of the gaseous or liquid silane or germane can be branched off or withdrawn by means of suitable pipelines, for example from a tank. The silane or germane can then optionally be transferred into the epitaxy reactor by means of an evaporator.

The measurement of the specific resistivity "at the surface" can be effected without or with pretreatment (for example by cleaning or polishing) directly at the surface, or else, for example after grinding, just beneath the original surface.

If only a single resistivity is determined in this variant of the process, it is possible to conclude only a total content of elements of main groups 3 and 5 of the periodic table of the elements without attributing the cause of the impurity to any elements.

If the impurity is, or the impurities are, to be attributable to the elements of main group 3 on the one hand and the elements of main group 5 of the periodic table on the other hand, the above-described process should be modified at least in steps d) and e), namely in that d) a profile of the specific resistivity as a function of the height of the layer is recorded by repeated measurement at different heights of the layer, measured from the original wafer surface, and e) the specific resistivities measured and recorded as a function of layer height are attributed to a degree of purity, including an attribution of the contaminating elements to main group 3 and/or 5 of the periodic table of the elements, the degree of purity preferably being reported as a concentration.

If, in this variant of the process, a resistivity profile has been established as a function of the height of the layer at which the resistivity has been measured, it is possible to conclude on the basis of the shape of the profile whether the element is one of main group 3 of the periodic table of the elements or one of main group 5 On this subject, see also FIG. 2 and the corresponding description of figures. An exact analysis of the shape of the profile can also enable determination of whether there is a mixture of elements of main groups 3 and 5 of the periodic table.

The measurement to be conducted in step d) is preferably effected to SEMI standards MF672 and MF674.

In steps e), the particular specific resistivity measured is then preferably converted to the charge carrier concentration. In the case that a resistivity profile is evaluated, the final resistivity is taken, i.e. the value which no longer changes with rising layer thickness but forms the final plateau (cf. FIG. 2). The conversions for this purpose may be according to Thurber, Mattis, Liu and Filiben (in: National Bureau of Standards Special Publication 400-64, *The Relationship between Resistivity and Dopant density for Phosphorus and Boron Doped Silicon*, May 1981). The charge carrier concentration (proportion by volume) can then be used, via the density of the material (as an approximation, the value for Si), to calculate the proportions by weight, for example in ppb or ppt. In the present case, the SSM 2000 resistivity measuring instrument (from Semilab) is used with the corresponding evaluation software supplied (analysis.exe). The evaluation software is programmed so as to report the charge carrier concentration directly.

The core of the process described here is thus that the purity of silanes and germanes is determined indirectly using specific resistivity measurement. In the typical case, the inventive use in the indirect determination of the purity of the silanes or germanes comprises the production of a silicon or germanium layer from at least some of the silane or germane and the simultaneous or subsequent measurement of the specific resistivity of this silicon or germanium layer.

The present invention further provides a plant for industrial production and/or industrial dispensing of silanes or germanes, said plant comprising a station for quality control of the silanes or germanes produced and/or provided for dispensing, characterized in that the station for quality control comprises an instrument for measurement of the specific resistivity of a silicon or germanium layer deposited on a surface. The inventive plant, the station for quality control and the instrument for measuring the specific resistivity are preferably configured such that the process described above can be performed in all its aspects.

Figure 1:
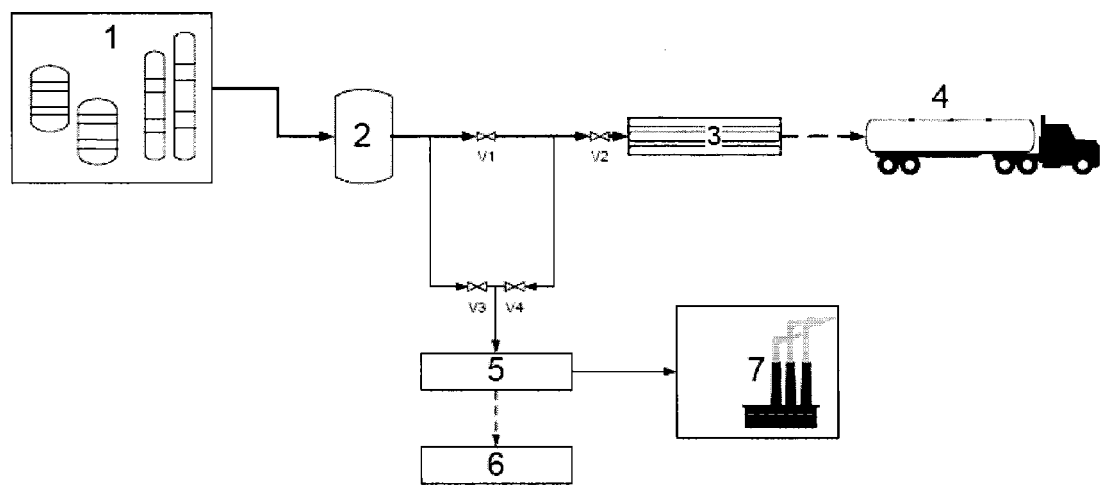
FIG. 1 shows a schematic of a production and dispensing plant for silanes or germanes including a station for quality control comprising an instrument for the measurement of the specific resistivity.
Figure 2:
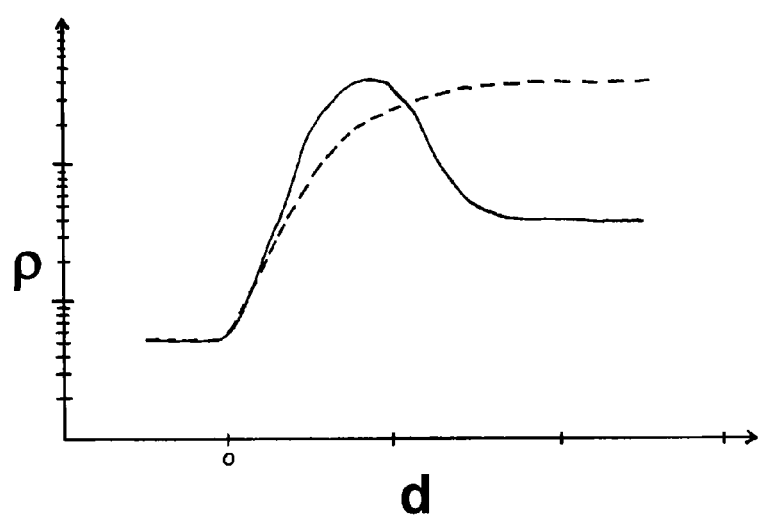
FIG. 2 shows a schematic of a typical curve profile for the dependence of the specific resistivity on the layer thickness for a p-type and for an n-type impurity.
Figure 3:
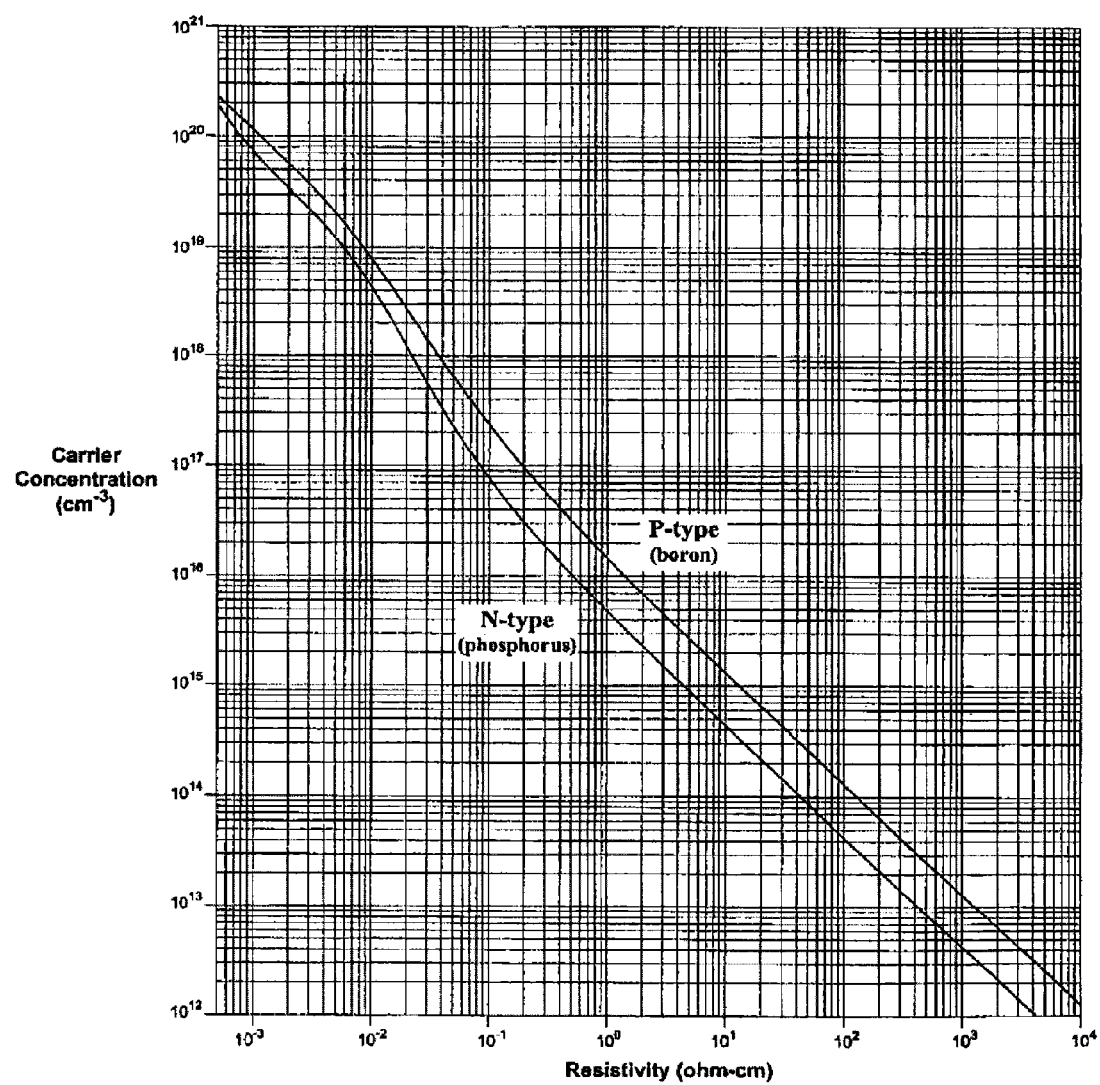
FIG. 3 shows the logarithmic plot of the charge carrier concentration in $cm^{-3}$ as a function of the specific resistivity in $\Omega cm$ for p-type impurities (e.g. boron) and for n-type impurities (e.g. phosphorus).

In the curve profiles shown in FIG. 2, typical curve profiles for the specific resistivity ρ are plotted against the layer thickness d. On the left-hand side <0, the constant specific resistivity of the substrate wafer is evident. With increasing epitaxial layer thickness, the resistivity rises and, in the case of the dotted line, approaches a limit/plateau. This is the case when wafer dopant and predominant impurity in the silicon or germanium layer deposited are of the same type, i.e. n-type or p-type. If wafer dopant and predominant impurity in the layer deposited differ, i.e. n-wafer/p-layer or p-wafer/n-layer, the result is the solid curve profile with a maximum at which dopant from the wafer and impurity in the layer just cancel one another out. Here too, a plateau is attained, which is determined only by the impurity/impurities from the silicon or germanium layer. It should be noted that the change in specific resistivity at the transition from the wafer to the layer is not abrupt, since the doping and contaminating elements migrate or diffuse across the interface to the other side. With knowledge of the wafer dopant, it is thus possible to determine whether the impurity is a p- or n-type impurity.

EXAMPLE 1

High-purity $SiCl_4$ was transferred from a reservoir tank via a line into an evaporator, which was in turn attached to the gas inlet of an ASM 2000 epitaxy reactor. The gaseous $SiCl_4$ was deposited in the presence of hydrogen (partial pressures: $H_2$ 1 bar, $SiCl_4 10^{-3}$ bar) at 1150° C. onto a 100 mm silicon wafer (p-type, approx. 30 $\Omega cm$) up to a layer thickness of 23 µm. The coated wafer was prepared according to SEMI MF 674 and then analysed according to SEMI MF 525/672 on an SRP instrument (SSM 2000). The curve profile did not have a maximum. The specific resistivity in the region of the plateau (cf. dotted curve in FIG. 2) was >100 $\Omega cm$. The curve profile leads to the conclusion of a p-type impurity such as boron. The charge carrier concentration was determined to be <1.5×10$^{14}$ $cm^{-3}$.

EXAMPLE 2

"Electronic grade" dichlorosilane was fed from a reservoir tank via a line to the gas inlet of an ASM 2000 epitaxy reactor. The gaseous dichlorosilane was deposited in the presence of hydrogen (partial pressures: $H_2$ 1 bar, $SiH_2Cl_2 10^{-3}$ bar) at 950° C. onto a 100 mm silicon wafer (p-type, approx. 30 $\Omega cm$) up to a layer thickness of 16 µm. The coated wafer was prepared according to SEMI MF 674 and then analysed according to SEMI MF 525/672 on an SRP instrument (SSM 2000). The curve profile had a maximum. The specific resistivity in the region of the plateau (cf. solid curve in FIG. 2) was >400 $\Omega cm$. The curve profile leads to the conclusion of an n-type impurity such as phosphorus or arsenic. The charge carrier concentration was determined to be <1.1×10$^{13}$ $cm^{-3}$.

EXAMPLE 3

High-purity monosilane was fed from a reservoir tank via a line to the gas inlet of an ASM 2000 epitaxy reactor. The gaseous monosilane was deposited in the presence of hydrogen (partial pressures: $H_2$ 1 bar, $SiH_4 10^{-3}$ bar) at 950° C. onto a 100 mm silicon wafer (p-type, approx. 30 $\Omega cm$) up to a layer thickness of 15 µm. The coated wafer was prepared according to SEMI MF 674 and then analysed according to SEMI MF 525/672 on an SRP instrument (SSM 2000). The curve profile did not have a maximum. The specific resistivity in the region of the plateau (cf. dotted curve in FIG. 2) was >800 $\Omega cm$. The curve profile leads to the conclusion of a p-type impurity such as boron. The charge carrier concentration was determined to be <1.7×10$^{13}$ $cm^{-3}$.

LIST OF REFERENCE NUMERALS (1) Production and purification
(2) Reservoir tank
(3) Dispensing
(4) Shipping
(5) Deposition (epitaxy)
(6) Specific resistivity measurement
(7) Incineration plant

The invention claimed is:
1. A process for indirectly determining purity, the process comprising:
   industrially producing and/or dispensing a silane or germane comprising impurities from main groups 3 and 5 of the periodic chart;
   extracting an amount of the silane or germane from the production and/or dispensing;

depositing, by chemical vapour deposition, a silicon layer or a germanium layer on a surface of a silicon or germanium wafer with at least a portion of the extracted amount of the silane or germane in a gaseous state, wherein the silicon layer or the germanium layer comprises impurities from main groups 3 and 5 of the periodic chart;

measuring a specific resistivity of the silicon layer or the germanium layer;

recording a profile of the specific resistivity as a function of a height of the silicon or germanium layer by repeated measurement at different heights of the layer, measured from an original wafer surface; and determining the purity based on the specific resistivity and at least one reference value, wherein specific resistivities measured and recorded as a function of layer height are attributed to a degree of purity, wherein the purity relates to a total content of elements of main groups 3 and 5, including an attribution to main group 3 and/or 5.

2. The process according to claim 1, comprising depositing the silicon layer with the gaseous silane to determine the purity of the silane,
wherein the silane is an unsubstituted mono-, di- or trisilane; or a singly, multiply or fully halogen-substituted mono-, di- or trisilane.

3. The process according to claim 1, wherein the purity includes an attribution to main group 3.

4. The process according to claim 1, wherein the purity includes an attribution to main group 5.

5. The process according to claim 1, comprising depositing the silicon layer with the gaseous silane onto the silicon wafer to determine the purity of the silane.

6. The process according to claim 5, wherein:
the silicon wafer is a doped wafer having a specific resistivity of <1000 Ωcm, and the silicon layer has a thickness of 5 to 100 µm; or
the silicon wafer is a lightly doped wafer having a specific resistivity of >1000 Ωcm, and the silicon layer has a thickness of 1 to 50 µm.

7. The process according to claim 1, wherein the process occurs repeatedly during the industrial production and/or dispensing.

8. The process of claim 1, which indirectly determines the purity of silanes and germanes.

9. The process according to claim 8, wherein the measuring of the specific resistivity occurs simultaneous with, or subsequent to, the depositing of the silicon layer or the germanium layer.

10. The process according to claim 1, comprising depositing the germanium layer with the gaseous germane to determine the purity of the germane,
wherein the gaseous germane is: an unsubstituted mono-, di- or trigermanes; or a singly, multiply or fully halogen-substituted mono-, di- or trigermane.

11. The process according to claim 1, comprising depositing the germanium layer with the gaseous germane onto the germanium wafer to determine the purity of the germane.

12. The process according to claim 11, wherein:
the germanium wafer is a doped wafer having a specific resistivity of <1000 Ωcm, and the germanium layer has a thickness of 5 to 100 µm; or
the germanium wafer is a lightly doped wafer having a specific resistivity of >1000 Ωcm, and the germanium layer has a thickness of 1 to 50 µm.

13. The process according to claim 1, comprising:
depositing a silicon layer on a surface with a gaseous silane; and then
measuring a specific resistivity of the layer and determining the purity of the silane based on the specific resistivity and at least one reference value.

14. The process according to claim 1, comprising:
depositing a germanium layer on a surface with a gaseous germane; and then
measuring a specific resistivity of the layer and determining the purity of the germane based on the specific resistivity and at least one reference value.

15. The process according to claim 2, wherein the gaseous silane is selected from the group consisting of $SiH_4$, $SiH_3Cl$, $SiH_2Cl_2$, $SiHCl_3$, $SiCl_4$, $Si_2H_6$, $Si_2Cl_6$, $Si_3H_8$, and $Si_3Cl_8$.

16. The process according to claim 10, wherein the gaseous germane is selected from the group consisting of $GeH_4$ and $GeCl_4$.

17. The process according to claim 1, wherein the purity includes an attribution to main group 3 and main group 5.

18. The process according to claim 1, wherein the thickness of the silicon layer or the germanium layer is such that the specific resistivity measured is influenced exclusively by the extracted silane or germane employed in the chemical vapour deposition.

* * * * *